(12) United States Patent
Büttgenbach et al.

(10) Patent No.: US 7,104,117 B2
(45) Date of Patent: Sep. 12, 2006

(54) DEVICE AND METHOD FOR DETERMINING THE QUALITY OF A MEDIUM, PARTICULARLY OF A LUBRICANT AND/OR COOLANT

(75) Inventors: Stephanus Büttgenbach, Sickte (DE); Hans-Heinrich Harms, Wolfenbüttel (DE)

(73) Assignee: Hydac Electronic GmbH, Saarbrücken (DE)

( * ) Notice: Subject to any disclaimer, the term of this patent is extended or adjusted under 35 U.S.C. 154(b) by 0 days.

(21) Appl. No.: 10/493,496

(22) PCT Filed: Oct. 15, 2002

(86) PCT No.: PCT/EP02/11517

§ 371 (c)(1),
(2), (4) Date: Apr. 22, 2004

(87) PCT Pub. No.: WO03/038394

PCT Pub. Date: May 8, 2003

(65) Prior Publication Data

US 2004/0250606 A1    Dec. 16, 2004

(30) Foreign Application Priority Data

Oct. 29, 2001    (DE)    ................. 101 52 777

(51) Int. Cl.
*G01N 33/26*  (2006.01)
*G01N 29/02*  (2006.01)
*G01N 25/00*  (2006.01)

(52) U.S. Cl. ............... 73/61.49; 73/53.05; 73/54.01; 73/54.02; 73/61.79; 73/64.53

(58) Field of Classification Search ............... 73/53.01, 73/53.05, 54.01, 54.02, 61.41, 61.49, 61.76, 73/61.79, 64.53
See application file for complete search history.

(56) References Cited

U.S. PATENT DOCUMENTS 6,223,588 B1 *    5/2001    Burgass et al. ............ 73/53.01

FOREIGN PATENT DOCUMENTS

| DE | 41 31 969 A1 | 4/1993 |
| DE | 44 00 838 A1 | 7/1995 |

(Continued)

OTHER PUBLICATIONS

J. M. Hammond, et al.; An Acoustic Automotive Engine Oil Quality Sensor, 1997 IEEE International Frequency Control Symposium, 1997, pp. 72-80, Department of Electrical and Computer Engineering, University of Maine, Orono, Maine 04469, USA; Control Devices Inc., Standish, ME 04084, USA.

(Continued)

*Primary Examiner*—Daniel S. Larkin
(74) *Attorney, Agent, or Firm*—Roylance, Abrams, Berdo & Goodman, L.L.P.

(57) ABSTRACT

A device (1) for determining the qualify of a medium, particularly of a lubricant and/or cutting oil, includes a number of sensors (3, 4, 5, 6, 7) that emit electric output signals according to the respective sensor-specific input variables. One sensor is a temperature sensor (7) that emits an output signal, which is essentially only dependent on the temperature (T) of the medium and is essentially independent of, in particular, the quality of the medium. At least one other sensor (3, 4, 5, 6) emits an output signal that is dependent on both the quality of the medium as well as the temperature (T) of the medium. The sensors (3, 4, 5, 6, 7) are placed on a shared substrate (2) that can be immersed in the medium. An associated process also determines the quality of a medium.

20 Claims, 3 Drawing Sheets

FOREIGN PATENT DOCUMENTS

| | | |
|---|---|---|
| DE | 196 44 290 A1 | 5/1998 |
| DE | 197 06 486 A1 | 8/1998 |
| DE | 197 10 358 A1 | 9/1998 |
| DE | 198 50 799 A1 | 5/2000 |
| DE | 101 08 576 A1 | 9/2001 |
| WO | WO 00/15118 A1 | 3/2000 |
| WO | WO 01/55718 A1 | 8/2001 |

OTHER PUBLICATIONS

Erich Uttenthaler, et al.; Ultrasensitive quartz crystal microbalance sensors for detection of M13-Phages in liquids, 2001 Elsevier Science B.V., Biosensors & Bioelectronics 16 (2001), pp. 735-742, Fraunhofer-Institute for Microelectronic Circuits and Systems, Hansastr. 27d, 80686 Munich, Germany.

* cited by examiner

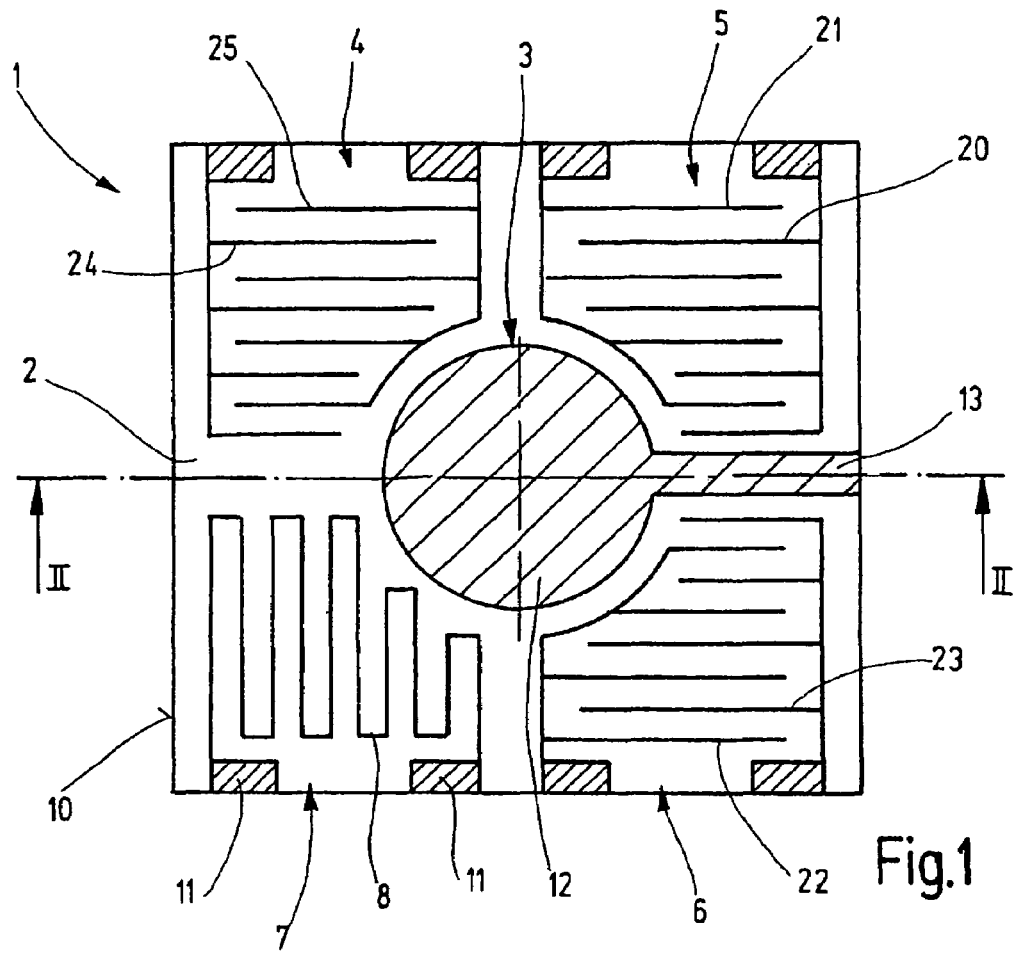
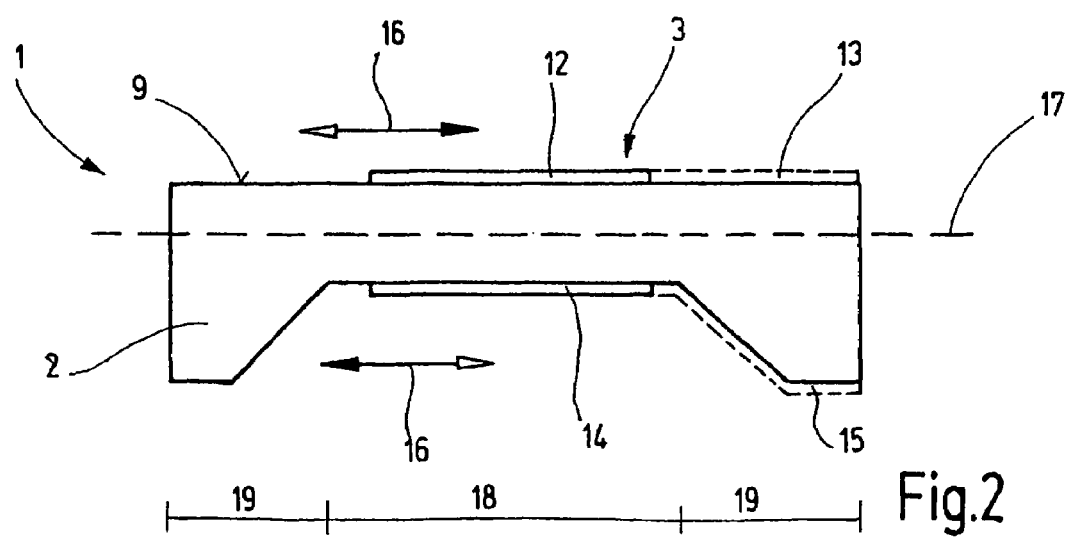

DEVICE AND METHOD FOR DETERMINING THE QUALITY OF A MEDIUM, PARTICULARLY OF A LUBRICANT AND/OR COOLANT

FIELD OF THE INVENTION

The present invention relates to a device and a method for determining the quality or properties of a medium, particularly of a lubricant and/or a coolant.

BACKGROUND OF THE INVENTION

Media, in the sense of the present invention, are frequently employed, particularly in drive technology, as lubricants and/or coolants. Properties of a medium are utilized which determine the quality of this medium, such as lowering the values of coefficients of friction. These properties are subject to internal and external influences, such as aging by light, air, operating temperature, stresses due to changes in temperature, impurities, etc. Proper operation requires a minimum quality of the medium, which must be replaced when the quality falls below this minimum. In practice the medium is replaced after expiration of a predetermined period of time or period of operation.

To the extent that sensors for obtaining parameters determining the quality of a medium have been disclosed in the art, it is a disadvantage that the output signal of these sensors also exhibits a high dependence on the temperature of the medium. If an attempt is made to eliminate this temperature dependence by measuring it through measurement of the parameter determining quality in the cold operating state, it is a disadvantage that this cold state does not as a rule correspond to the actual operating state in which the quality of the medium is a decisive factor.

DE 41 31 969 A1 discloses a lubricant oil monitoring device which records the parameters of pressure, temperature, and viscosity of a lubricant oil in situ. The proportion of lubrication-relevant long-chain molecules in relation to the proportion of the molecules already "used," and accordingly the viscosity of the lubricant oil, are determined from measurement of the relative permittivity. The data required for this purpose is made available from the experimentally determined relationship between the relative permittivity and the technical lubricity of the oil in a storage unit.

DE 197 06 486 A1 discloses a device and a process for determining the state of aging of liquid media. At least one parameter of state of the liquid medium is determined during a first period, during which the liquid medium is in the initial state, and during at least a second period subsequent in time. The two states as determined are compared with each other. The state of the liquid medium is determined from the result of this comparison.

DE 198 50 799 discloses a sensor configuration for determining physical properties of liquids. Surface waves are excited and detected by electroacoustic converters on the polished surface of a substrate plate of uniform thickness of a piezoelectric material. The viscosity of the medium to be studied may be found from the propagation characteristic of the surface waves.

DE 101 08 576 A1 discloses a process and a device for temperature compensation of a piezoelectric device used as an actuator, for example, as positioning or drive device of a valve control system.

SUMMARY OF THE INVENTION

Objects of the present invention are to provide a device and a process for determining the quality of a medium, a lubricant and/or coolant oil in particular, which overcomes the disadvantages of the state of the art.

Other objects of the present invention to provide a device and a process for determination of the quality of the medium, even when the temperature of the medium is higher than the ambient temperature.

These objects of the present invention are basically attained by a device for determining the quality of a medium, a lubricant and/or coolant in particular, such as a lubricant and/or coolant oil, where the device has a plurality of sensors immersible in the medium. The sensors generate an electric output signal as a function of the respective sensor-specific input value. One sensor is a temperature sensor which emits an output signal depending more or less only on the temperature of the medium, and in particular is more or less independent of the quality of the medium. At least one other sensor generates an output signal which depends both on the quality of the medium and on the temperature of the medium. The plurality of sensors are mounted on a common substrate, and consequently, are thermally connected to each other.

The medium may be represented either by a gas or by a liquid, such as a liquid produced from a renewable primary product.

Since the output signal of the temperature sensor is more or less independent of the quality of the medium, the influence of temperature is registered and emitted separately as a measured variable. This measured temperature value may be taken into account appropriately in evaluation of the output signal of the other sensors, in which the temperature occurs as a disturbance variable. Mounting the sensors on a common substrate ensures good thermal coupling of the two sensors, and ensures that the temperature measured by the temperature sensor is more or less identical to the temperature of the other sensor. This arrangement is particularly advantageous over a corresponding device in which the temperature sensor and the other sensor are configured as discrete structural elements, which in addition are separated from each other by a significant distance in space.

The sensors preferably are miniaturized by thick-layer, hybrid, or preferably by thin-layer technology, so that the spacing of the temperature sensor from the other sensor amounts to a few millimeters, for example, is less than 5 mm. This spacing ensures, even in the event of flows in the medium, that the temperature sensor and the other sensor will always be more or less at the same temperature, that of the medium.

The temperature sensor preferably is a resistance thermometer. The resistance path of the temperature sensor is applied to the substrate and is electrically insulated from the medium, but does not have good thermal coupling to the medium. For example, the resistance path is covered by a very thin layer of an electrically insulating material. The thinner this layer, the smaller is its thermal capacity and the faster the temperature sensor reacts to temperature changes in the medium. The use of a resistance thermometer is an advantage, since, as a result relatively low-resistance output, signals may be provided with high immunity to interference, in particular to electromagnetic interference pulses. For example, a current may be impressed into the resistance thermometer and the voltage dropping on the temperature sensor is a gauge of the temperature. To obtain sufficiently high signal voltages even with low currents and consequently low self-heating, the metal resistance path preferably is applied to the substrate as a structured thin layer in the form of a meander.

The other sensor may, for example, be an electrically excitable mechanical oscillating element. The resonance frequency of the other sensor depends on damping by the medium, which in turn is a parameter for the quality of a medium. The damping depends on the viscosity and density of the medium. The oscillating element consequently measures a quantity depending on the viscosity or density, especially a quantity proportional to this property. As an alternative or in addition, the excitation to oscillation may be effected in another manner, such as by acoustic, optical, or the like means. Damping of different intensity modifies the resonance frequency, which typically falls within the range of a few to several 10 MHz. The mechanical oscillating element may be in different geometric configurations, including, for example, the form of a fork (tuning fork). However, laminar or disk-shaped substrates having electrodes for generation of oscillations on surfaces opposite each other are particularly simple and rugged.

The substrate is for this purpose preferably piezoelectric, that is, application of an electric field results in displacements in the crystal, and as a result, in changes in the shape of the substrate. Crystals of quartz ($SiO_2$) from which substrates are cut in a so-called AT cut are especially well suited. When the electrodes are mounted on opposite surfaces of the substrate thickness shear oscillations occur, the resonance frequency of which is the higher, the thinner is the substrate. Typical substrate thicknesses fall within the range of 10 to 500 µm, around 100 µm, for example. The resonance frequency may be raised by preferably local thin engraving. The quality of the oscillating element is generally lowered as a result.

The relationship between the measuring signal, that is, the displacement $\Delta f$ of the resonance frequency $f$, the thickness $d$, and the quality $Q$ of the thickness shear oscillator is generally such that the displacement $\Delta f$ increases with the resonance frequency. Specifically, the sensitivity increases with rising resonance frequency $f$. The resonance frequency $f$ increases with decreasing thickness $d$, for example, $f\sim1/d$. The quality drops with increasing resonance frequency $f$, for example, $Q\sim1/f$. The lower the quality, the greater is the noise restricting measurement resolution. These relationships yield the following optimization process in configuration of the device. First the thickness $d$ of the oscillating element is reduced, with the resonance frequency $f$ thereby increased. The difference in the test signals for new and used medium is consequently greater. Since the quality $Q$ of the oscillating element decreases, the noise grows stronger and the measurement error in determination of the resonance frequency $f$ increases. The optimum thickness $d$ is to be determined for each application from these parameters.

As an alternative or in addition, the device may have a second other sensor for determination of the relative permittivity of the medium. Permittivity may be evaluated as a measurement of the quality of the medium, for example, as a result of concentration of moisture and/or abraded particles. This second other sensor preferably is also applied to the substrate by the thin-layer method. Although electric insulation of the comblike meshing or dovetailing electrodes of the capacitor is not absolutely necessary, it is advantageous for many applications. As in the case of the resistance thermometer, insulation may be provided by an electrically insulating thin cover layer.

As an alternative or in addition, a third other sensor is mounted on the substrate and comprises a conductance value sensor by means of which the electric conductance value of the medium may be determined. This value may be altered by concentration of abraded metal particles or by change in the acid components of a fluid, for example, the value may increase. The electrodes of the conductance value sensor are also applied to the substrate by the thin-layer method and come into contact with the medium, for example, by way of electrodes laterally intermeshing comblike and dovetailing electrodes.

As an alternative or in addition, a fourth other sensor is mounted on the substrate and comprises a moisture sensor. The electrodes of the moisture sensor are also applied by the thin-layer method and are covered by a moisture-absorbing layer. In some instances, moisture from the medium settles into this layer and thereby alters the dielectric properties of the layer, for example, one which is made of a polymer plastic.

The objects of the present invention are also basically attained by a process for determining the quality of a medium by use of a device, where the output signals of the sensor are transmitted to an evaluating device which compares the output signal of the other sensor to an expected value dependent on the temperature of the medium and which emits an output signal indicating the result of the comparison.

The respective temperature at which the output signal of the other sensor is compared with the associated expected value may be assigned as a fixed value, and in particular, may be a temperature which is reached in each cycle of operation, for example, 40° C. Thus, for example, in the case of an internal combustion engine in the operating cycle of which the temperature of the medium rises from the ambient temperature to approximately 80° C., every time the assigned temperature is reached, the output signal of the other sensor is compared with the expected value to permit arrival at an indication of the quality of the medium.

As an alternative, a corresponding expected value may be stored in the evaluating device for virtually any temperature reached by the medium in an operating cycle. Such expected values may be predetermined and may be found empirically, for example. In addition, these expected values may be calculated optionally on the basis of a predetermined initial value, with account taken of the pattern of the temperature of the medium over time, and accordingly, may be variable. For example, different operating cycles with different individual operating periods may be considered, ones which exert a different effect both on the quality of the medium and on the output signal of the other sensor.

Lastly, information may be stored in the evaluating device so that a measured output signal of the other sensor still determines a sufficiently high quality of the medium for one specific pattern of temperature over time, while the same output of this sensor represents a quality of the medium for another pattern of the temperature of the medium over time. The associated expected values preferably are storable in the evaluating device, which has a microprocessor and associated electronic storage means.

It is especially advantageous for a plurality of other sensors to be mounted on the substrate. The output signals of the other sensors determine other parameters of the medium, each of which is compared with associated expected values. If, for example, a resonance frequency of the mechanical oscillating element determines the viscosity, a capacitor determines the relative permittivity, a conduction value sensor determines the conductivity, and a moisture sensor determines the moisture content of the medium, a decision may be made on the basis of these four parameters if the quality of the medium is still adequate, and accordingly, which output signal is to be emitted.

This decision may be made simply in accordance with the majority of the output signals of the other sensors, for example, if at least three of the four other sensors emit a corresponding output signal. As an alternative, the output signal which indicates that the quality of the medium is no longer sufficient or at least is critical may also be made to depend on emission of a corresponding output signal by a specific one of the other sensors, such as the mechanical oscillating element. As another alternative, the decision criteria may also be made to depend on the pattern of the temperature of the medium over time. In many applications, it suffices for the output signal to be displayed to distinguish only among "GOOD," "AVERAGE," or "POOR."

Other objects, advantages and salient features of the present invention will become apparent from the following detailed description, which, taken in conjunction with the annexed drawings, discloses preferred embodiments of the present invention.

BRIEF DESCRIPTION OF THE DRAWINGS

Referring to the drawings which form a part of this disclosure:

FIG. 1 is a top plan view of a device according to an embodiment of the present invention;

FIG. 2 is a side elevational view in section, taken along line of II—II the device in FIG. 1;

DETAILED DESCRIPTION OF THE INVENTION

Figure 3:
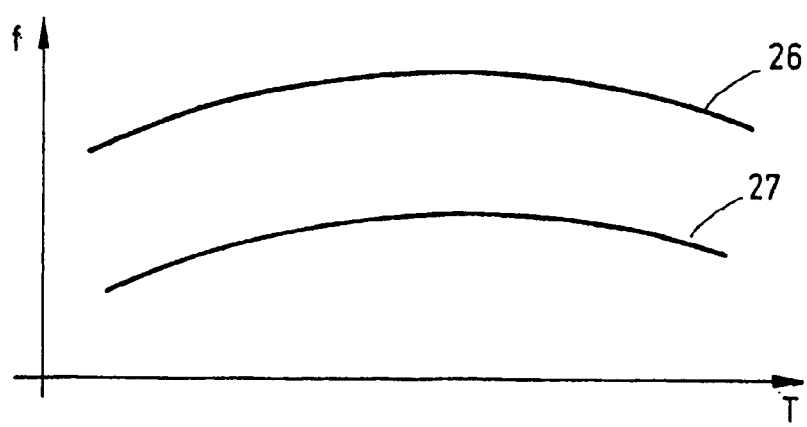
FIG. 3 is a graphical representation of typical variation of the resonance frequency f of the oscillating element with the temperature T of the medium.

FIG. 1 is a top plan view of a device 1 according to an embodiment of the present invention for determining the quality of a medium, a lubricant and/or coolant oil in particular. A plurality of sensors 3, 4, 5, 6, 7 are mounted on a common substrate 2 immersible in the medium. Each sensor emits an electric output signal as a function of the respective sensor-specific input value.

One sensor is a temperature sensor 7, which emits an output signal which is a function more or less exclusively of the temperature T of the medium and which is more or less independent of the quality of the medium. At least one other sensor 3, 4, 5, or 6 emits an output signal which depends both on the quality of the medium and on the temperature T of the medium. All sensors 3, 4, 5, 6, 7 are very efficiently thermally interconnected as a result of the configuration as thin-layer sensors and mounting on the common substrate 2.

The temperature sensor 7 is a resistance thermometer having a resistance path 8 applied to the substrate 2 in the form of a meander. The substrate 2 is a single-crystal quartz, with an AT cut. The surface 9 of the substrate forms an xz plane. The substrate 2 preferably is rectangular, and is square in the exemplary embodiment illustrated. The length of one edge 10 typically ranges from 2 to 20 mm, and preferably is around 5 mm. The edge 10 typically is inclined more or less 35° relative to the crystallographic z axis in the direction of the x axis. The thickness of the substrate 2 typically ranges from 50 µm to 1 mm, preferably from 100 to 200 µm.

In one embodiment of the present invention, the substrates 2 are purchased as semifinished products with assignable overall dimensions. Both substrate sides have a metal coating which subsequently is structured by photolithographic means, which may serve as a mask in preferably wet-chemical etching, which may serve, above all, as a conductor path and electric connecting surface. The metal coating preferably is a chromium/gold layer, the chromium essentially acting as a thin bonding agent for the gold layer on the quartz substrate. The gold layer provides the actual conductivity and is corrosion-resistant.

Preferably, a plurality of devices 1 according to the present invention are produced on a single quartz plate "in use". After completion of the thin-layer structuring, the plate is separated into the devices 1, for example, by abrasive grinding or sawing. The separated devices 1 may be mounted on a carrier board, such as one of epoxy resin, and connected to conductor paths provided there. The electric contact points and conductor paths may be sealed, to the extent possible, for example, with an epoxy adhesive. As a result, a reverse side of the substrate 2 may delimit a ventilatable space sealed off from the medium. Consequently, even pressurized media may be reliably evaluated. Damping of the oscillating element due to the carrier board or an enclosed volume of gas or fluid falsifying the result is prevented.

The temperature sensor 7 is designed as a resistance thermometer with a resistance path 8 in the form of a meander through which the two connecting electrodes 11 of the temperature sensor 7 are connected to each other. The thickness of the resistance path 8 ranges from 20 to 1000 nm, preferably from 100 to 500 nm, especially around 250 nm. Typical metal film resistors of the order of magnitude of 0.1 ohm are obtained as a result. The length selected for the meander preferably is such that a resistance of 200 ohm to 2 kiloohm is obtained as a result. This structure makes it possible, for example, when a current of 1 mA is impressed, to achieve an output voltage of the order of magnitude of 1 volt, a voltage which is sufficiently low and yet prevents self-heating of the temperature sensor 7 which would disturb the measurement.

Because of the temperature dependence of the specific resistance of the resistance path 8, which in the case of pure metals amounts to around 0.4 percent per degree Celsius and may be increased by additives, change in the output voltage of the temperature sensor 7 is a gauge of the temperature of the substrate 2 and accordingly of that of the medium. In order to isolate the resistance path 8 electrically from the medium after the resistance path 8 has been structured, the substrate is coated with a preferably inorganic insulating layer, preferably by plasma-supported precipitation of $SiO_2$ from the gas phase (PEC VD-$SiO_2$). The layer thickness selected is great enough only so that electric insulation of the resistance path 8 is ensured. On the other hand, the cover layer must be as thin as possible in order to guarantee good thermal coupling of the resistance path 8 to the medium. Favorable values for the thickness of the protective layer range are from 100 nm to 1000 nm, preferably are from 300 nm to 600 nm.

Mounted in the center of the surface 9 of the front side of the substrate 2 is a round metal electrode 12, the type and layer thickness of which preferably correspond to that of the resistance path 8. Electrode 12 may be produced simultaneously with resistance path 8. A connecting path 13 by way of which the electrode 12 may come into electric contact with the edge of the substrate 2 is extends from electrode 12 to one of the edges 10.

FIG. 2 presents a section II—II through the device 1, in particular through the substrate 2 shown in FIG. 1. For the sake of clarity only the metal coating of the electrode 12 or connecting path 13 is shown on the surface of the front side of the substrate 2. Another electrode 14 with which contact may be established by way of another connecting path 15, preferably from the same edge 10 of the substrate 2 as that of the electrode 12 on the surface 9, is mounted on the surface 9 forming the reverse side opposite the front side, in the area corresponding to the electrode 12. When alternating-current voltage is applied, the substrate 2 is excited to execute oscillations, in the exemplary embodiment illustrated by use of an AT cut in the form of a thickness shear oscillator, as indicated by the arrows 16. The movement nodes of this thickness shear oscillation are situated more or less in the neutral zone indicated by the broken line 17 and extending in the substrate 2.

In the exemplary embodiment illustrated, the substrate 2 was thin etched locally, in the center in particular, preferably by anisotropic wet-chemical etching, so that the substrate 2 is thinner in a first area 18 in which the electrodes 12, 14 are mounted than in a second area 19 adjoining the first area 18 and in particular surrounding the first area 18. The masking for the local thin etching preferably is effected by metal coating of the substrate 2, which may also be used to form the electrodes 12, 14 or, for example, the resistance path 8.

In the exemplary embodiment shown in FIG. 1, other sensors 4, 5, 6 are mounted on the surface 9 which, in addition to depending on the temperature T of the medium, depend on the parameters determining the quality of the medium.

The relative permittivity of the medium may be determined by capacitor 5. The capacitor 5 has for this purpose meshing comb electrodes 20, 21 insulated from each other and formed from the material of the resistance path 8. A typical width of the conductor paths of the comb electrodes 20, 21 ranges from 5 to 50 μm, and around 20 μm in particular. The number and length of the comb electrodes 20, 21 determines the base capacitance of this sensor 5. The value selected for the base capacitance which must not for measurement engineering reasons be too small. This base capacitance typically ranges from 2 and 20 picofarad, preferably between 5 to 10 picofarad. It is advantageous to provide for this purpose 20 to 200 such comb electrodes 20, 21, in particular 30 to 50 comb electrodes. An electrically insulating coating of the electrodes 20, 21 would not be absolutely necessary for the capacitor 5, but would in many instances nevertheless be advantageous and harmless, since the capacitance per unit length caused by the coating is low. On the other hand, the coating protects from corrosion more or less independently of the temperature.

In addition to the capacitor 5, a conductance sensor 6 is mounted on the substrate 2. The sensor also has meshing comb electrodes 22, 23 and is identical in structure to that of the capacitor 5, except for the difference that these electrodes have no electrically insulating coating. Rather, electrodes 22, 23 establish electric contact with the medium.

The resistance values to be expected range in the case of a typical medium, especially in the case of a lubricant obtained from renewable primary products, one such as rapeseed oil, from 1 megohm to 20 megohm, for example, approximately 5 megohm. The measurement frequency should be high enough so that resistance values may be determined reliably even at lower temperatures. On the other hand, the measurement frequency selected should not be too high, since otherwise the influence of the quality of the medium on the resistance value does not make itself so distinctly felt. Favorable measurement frequencies range from 100 Hz to 1 MHz, preferably from 1 kHz to 100 kHz.

In measurement of the conductivity, as in measurement of the capacitance, measurements at different frequencies may also be advantageous, since different contaminants may affect the conductivity and the relative permittivity differently in different frequency ranges. Measurement with alternating signals has the advantage that electrochemical processes are more or less excluded from the medium.

Also mounted on the substrate 2 is a moisture sensor 4. The meshing comb electrodes 24, 25 of the moisture sensor are also identical to those of the capacitor 5 in structure, but in this case are of course provided with a cover layer absorbing moisture, a layer of a polymer plastic, for example. Absorption of moisture in the cover layer causes change in the measurable capacitance per unit length, so that the capacitance value measured for the moisture sensor 4 is a gauge of the percentage of moisture in the medium and so of the quality of the medium.

The connecting paths of all sensors 3, 4, 5, 6, 7 preferably are mounted along an edge 10 of the substrate 2, where they form corresponding connecting surfaces (pads). By the connecting surfaces, the external connecting lines may be connected to a carrier board. With the exception of the electrodes of the oscillating element 3, the connecting surfaces of the sensors 4, 5, 6, 7 are mounted on two opposite edges 10 of the substrate 2.

The device 1 is immersed in the medium and is mounted on a carrier board so that only the electrode 12 on the front side 9 comes into contact with the medium. For this purpose, the electrode 12 preferably is connected to the ground potential to prevent electrochemical processes in this medium.

The other electrode 14, on the reverse side of the substrate 2 also should not touch the carrier board in the case of unetched substrates 2. Rather, electrode 14 should be positioned a sufficient distance from the carrier board, since otherwise additional damping occurs. On the whole, the device 1 should be mounted on a carrier board so that the freest possible oscillation of the oscillating element 3 is ensured. For example, the substrate 2 should be rigidly clamped only on the edges 10, and even there only at certain points. Should the medium to be studied be under significant pressure, this pressure is also to be taken into account in evaluation of the output signals of the device 1.

FIG. 3 illustrates the typical pattern of the resonance frequency f of the oscillating element 3 as a function of the temperature T of the medium in the range of 25 to 80° C. The calibration curve 26 represents unused medium. The calibration curve 27 represents the same medium after 1000 hours of operation. The standard deviations associated with the measured values of the calibration curves 26, 27 tend downward with rising temperature. As a result, the difference with respect to the quality of the oil at higher temperatures, in the area of 60° C. and higher, for example, can be more reliably detected. The calibration curves 26, 27 were determined with a device 1, the substrate 2 of which was thin-etched locally. The associated resonance frequency f was in the area of approximately 50 MHz. The changes in the resonance frequency f above the temperature range indicated were of the order of magnitude of approximately 20 kHz.

The sensitivity of the oscillating element 3 is also decisive in determining the spacing of the two calibration curves 26, 27. The higher the sensitivity of the oscillating element 3, the greater the difference between the measured values for unused and used medium. The noise fraction of the resonance frequency f also increases with an increase in the resonance frequency f. Resonance frequencies f ranging from 10 to 50 MHz, preferably such frequencies around approximately 20 MHz, have been found to be favorable.

Figure 4:
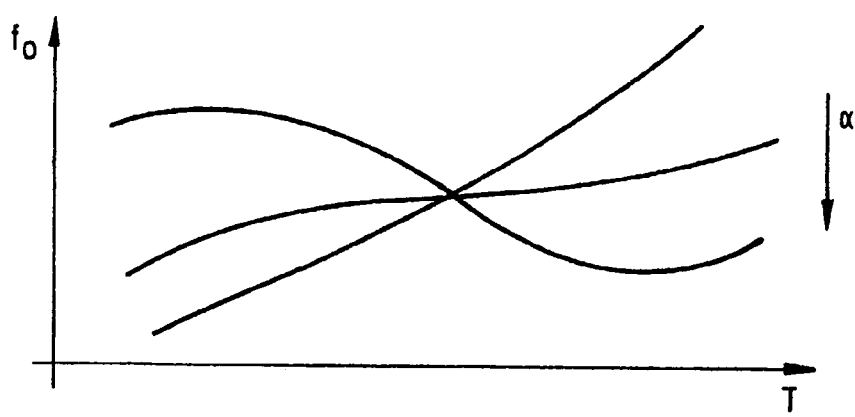
FIG. 4 is a graphical representation of various values of the base frequency $f_o$ as a function of temperature.

The pattern of the calibration curves 26, 27 is also determined by the pattern of the temperature dependence of the base frequency $f_o$ of the oscillating element 3, that is, without surrounding medium. FIG. 4 illustrates various temperature dependencies of the base frequency $f_o$, the angle α of the crystal cut being the parameter of the group of curves shown. Choice of an appropriate angle α permits adjustment of the calibration curves 26, 27. The spacing of the calibration curves 26, 27 at a given temperature T is more important with respect to determination of the quality of the medium than the respective pattern of such curves above temperature T.

Figure 5:
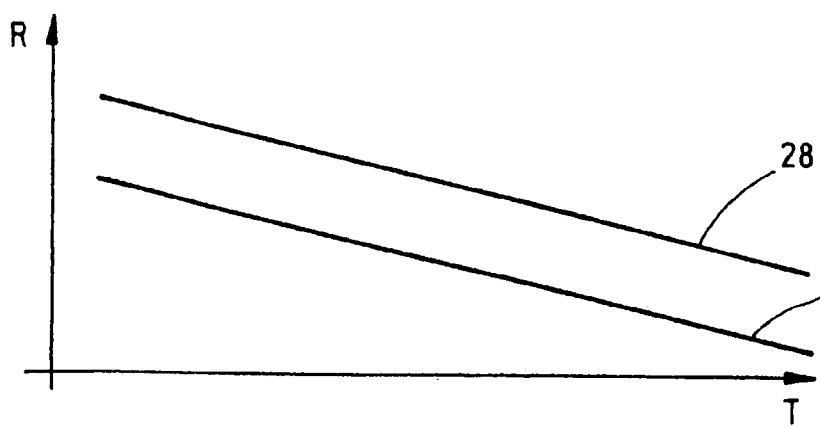
FIG. 5 is a graphical representation of a pattern of the electric resistance R with variation in temperature T, as measured by the conductance sensor.

FIG. 5 illustrates a typical pattern of the electric resistance R above temperature T measured by the conductance sensor 6. Calibration curve 28 represents unused medium. Calibration curve 29 represents the medium after a period of operation of 1000 hours. The resistance R drops and the electric conductivity of the medium rises with decrease in the quality. The measurement frequency is approximately 10 kHz. The resistance values of the unused medium dropped from around 50 megohm at 20° C. to around 20 megohm at 80° C.

Figure 6:
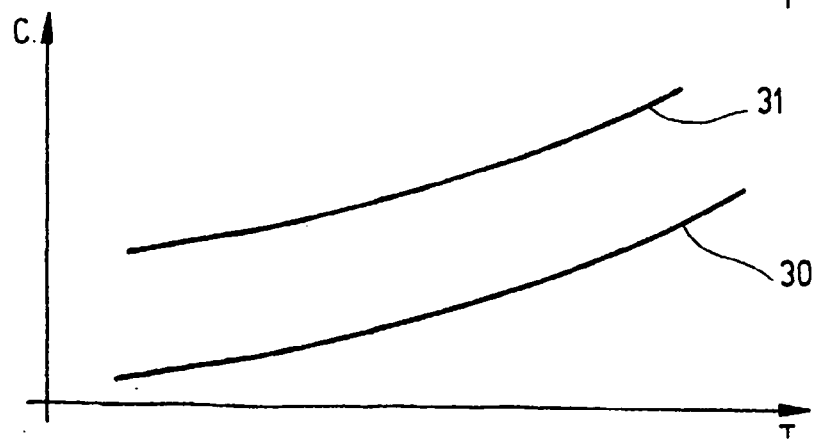
FIG. 6 is a graphical representation of variations of the measured capacitance C with variation in the temperature T.

FIG. 6 illustrates the pattern of variation in the capacitance C of the medium as a function temperature T as measured by the capacitor 5. Calibration curve 30 represents the measured values of the unused medium. Calibration curve 31 represents the measured values of the medium after 1000 hours of operation. The capacitance of the medium increases with decrease in quality. The capacitance values were determined at a measurement frequency of 100 kHz, at which sufficiently stable measurement results are obtained. The capacitance values, for example, range from about 5.5 picofarad at 20° C. to about 6.5 picofarad at 80° C. The capacitance values of the medium increase significantly over the entire temperature range with increase in the period of operation.

Figure 7:
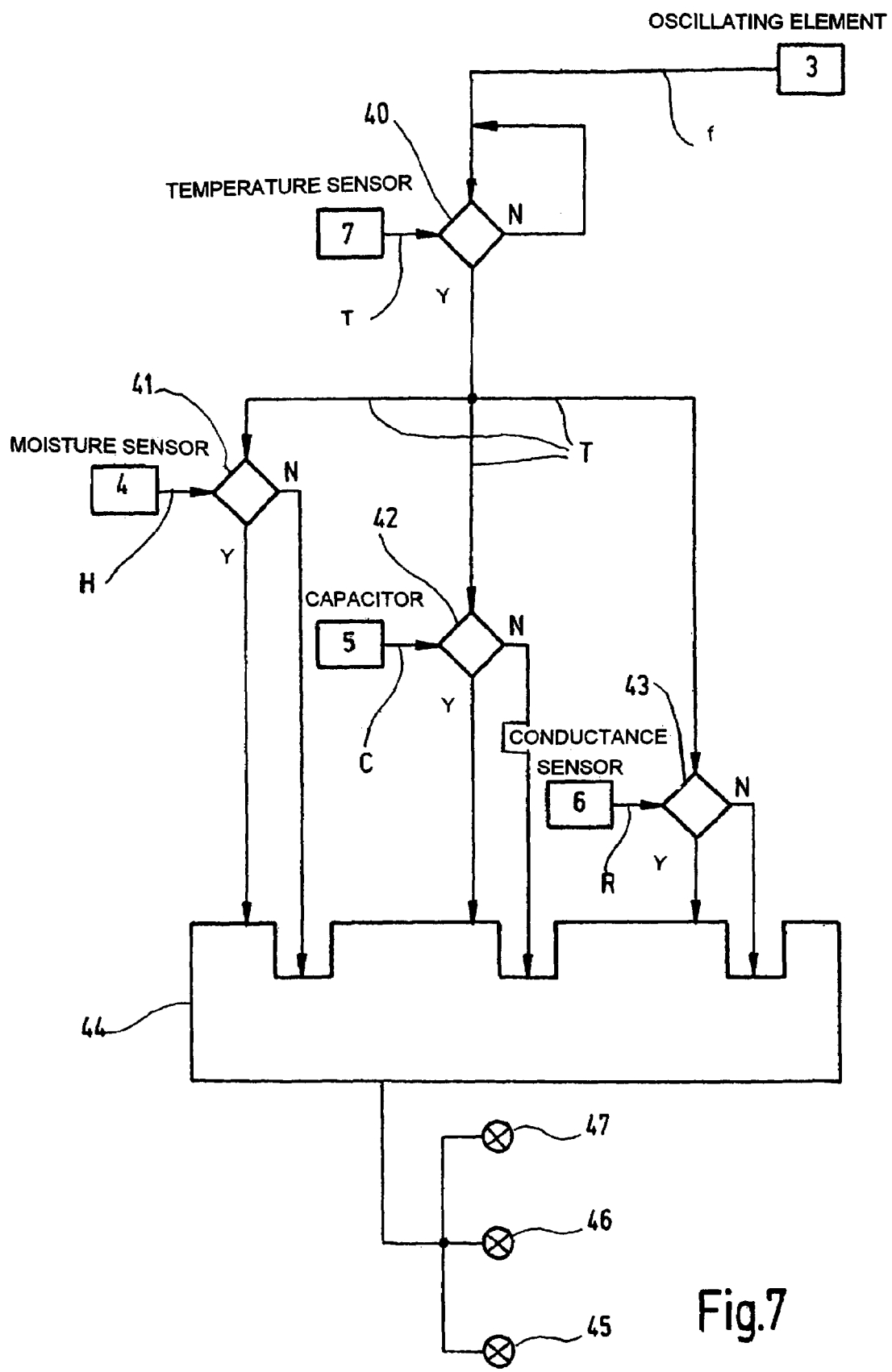
FIG. 7 is a flow chart of the process according to an embodiment of the present invention.

FIG. 7 presents a diagram of the process of the present invention. The resonance frequency f of the oscillating element 3 is delivered, together with the temperature T of the medium determined by the temperature sensor 7, to a first test step 40. A test is carried out to determine if the measured resonance frequency f is an indication of a lower or even deficient quality of the medium. If the result of this test is NO (N), the first test step 40 is repeated permanently or at assignable time intervals. If, on the other hand, the result of this test step is YES (Y), another test of the quality of the medium is carried out.

For this purpose the output signals of the other sensors, in the exemplary embodiment illustrated, those of the moisture sensor 4 (moisture H), the capacitor 5 (capacitance C), and the conductance sensor 6 (resistance R), are compared with the associated expected values stored in the evaluating unit, in test steps 41, 42, 43 either simultaneously or in immediate succession, account being taken of the temperature T determined by the temperature sensor 7. The results of these YES/NO (Y/N) comparisons are delivered to the evaluating circuit 44 and are there evaluated in accordance with an assignable evaluating key.

For example, the evaluation key may be used to determine that, if none of the other test steps 41, 41, 43 signals that an expected value has been obtained, and accordingly shows no significant impairment of the quality of the medium, the evaluating circuit 44 emits an output signal which indicates a sufficiently high quality of the medium, for example, by lighting a green signal lamp 45, a corresponding light emitting diode (LED), for example. Should one of the test steps 41, 42, 43 indicate that a respective associated expected value has been obtained, the evaluating circuit 44 lights a yellow signal light 46. Should two of the test steps 41, 42, 43 signal that an expected value has been reached, the red signal light 47 lights and in addition the evaluating circuit may emit an acoustic signal.

Should all three test steps 41, 42, 43 signal that the associated expected value has been reached, the evaluating circuit 44 may cause switching off of the associated device, or in any event may prevent reconnection or at least make it depend on acknowledgment of the associated alarm signal.

Various criteria for evaluation of the results of the test steps 41, 42, 43 are possible, depending on the respective application. Other sensors may, of course, also be mounted on the substrate 2 of the device 1, ones which make additional test steps possible. The evaluating circuit 44 has a corresponding number of input channels and connection options, and preferably is designed as programmable control unit in which a microprocessor is used.

Special importance is assigned to measurement of the resonance frequency in the exemplary embodiment described in the foregoing. It optionally forms a trigger for subsequent measurements. The other sensors may perform this function as an alternative or in addition to measurement of the resonance frequency.

For many applications, however, it is advantageous for none of the sensors to occupy such a preferred position and for all other sensors, except the temperature sensor, to be on an equal footing.

An alternative evaluating key, for example, presents the aspect that two threshold values are established for every parameter. The variation of the measured signals, and accordingly the parameters over time, is monitored. The parameter having a value below the first respective threshold value is completely unobjectionable. The parameter is higher, but not yet a critical value, between the first and the second threshold value. A parameter value above the second threshold value is critical.

If several parameters are determined by one other sensor, exceeding of the second threshold value of a single parameter results in triggering of the alarm or lighting of the red signal light 47. The yellow signal light 46 is lit if no parameter exceeds the second threshold value and a plurality of the parameters exceed the respective first threshold value. The green signal light 46 is lit if none of the parameters exceeds the respective second threshold value, and a plurality of the parameters fail to exceed even the first threshold value.

While various embodiments have been chosen to illustrate the invention, it will be understood by those skilled in the art that various changes and modifications can be made therein without departing from the scope of the invention as defined in the appended claims.

What is claimed is:

1. A device for determining changes in properties of a fluid medium from ideal fluid properties to actual fluid properties, comprising:
   a temperature sensor emitting an output signal consisting essentially only of a function of temperature of the medium and being essentially independent of other properties of the medium;
   a first sensor emitting an output signal which is a function both of the temperature of the medium and viscosity of the medium, said first sensor being an electrically oscillating element; and
   a common substrate on which said sensors are mounted and being immersible in the medium, said substrate being piezoelectric, having oppositely facing sides and having electrodes on said oppositely facing sides for excitation of oscillations, said substrate forming said oscillating element.

2. A device according to claim 1 wherein
said temperature sensor is a resistance thermometer having a resistance path mounted on said substrate, being electrically insulated from the medium and having a good thermal coupling with the medium.

3. A device according to claim 2 wherein
said resistance path is mounted as a structured thin layer in meander form.

4. A device according to claim 1 wherein
said oscillating element has a resonant frequency that is a function of the viscosity of the medium.

5. A device according to claim 1 wherein
said substrate comprises a quartz plate formed by an AT cut from a quartz crystal.

6. A device according to claim 1 wherein
said electrodes are centered on opposite sides of said substrate.

7. A device according to claim 1 wherein
said substrate has first and second areas, said substrate being thinner in said first area than in said second area, said second area surrounding said first area.

8. A device according to claim 1 wherein
said substrate comprises a surface in contact with the medium.

9. A device according to claim 1 wherein
a reverse side of said substrate delimits a ventilatable space sealed off from the medium.

10. A device according to claim 1 wherein
another sensor is mounted on said substrate, and comprises a capacitor for determining relative permittivity of the medium.

11. A device according to claim 10 wherein
said capacitor comprises laterally meshing comb electrodes electrically insulated from one another, mounted on said substrate as a structured thin layer and electrically insulated from the medium.

12. A device according to claim 1 wherein
another sensor is mounted on said substrate, and is an electric conductance sensor for determining electrical conductance of the medium.

13. A device according to claim 12 wherein
said electric conductance sensor comprises laterally meshing comb electrodes electrically insulated from each other, mounted on said substrate as a structured thin layer and established in electrical contact with the medium.

14. A device according to claim 1 wherein
another sensor is mounted on said substrate and is a moisture sensor for determining moisture content of the medium.

15. A device according to claim 14 wherein
said moisture sensor comprises laterally meshing comb electrodes electrically insulated from each other, mounted on said substrate as a structured thin layer, and covered by and separated from the medium by a moisture-absorbing layer.

16. A process for determining changes in properties of a fluid medium, the process comprising the steps of:
   immersing a piezoelectric substrate having a temperature sensor and a viscosity sensor mounted thereon;
   emitting a temperature output signal from the temperature sensor consisting essentially only of a function of temperature of the medium and being essentially independent of other properties of the medium;
   emitting a viscosity output signal from the viscosity sensor which is a function both of the temperature of the medium and viscosity of the medium by electrically exciting an oscillating element formed by the substrate having electrodes mounted on opposite surfaces thereof;
   comparing said output signals in an evaluating circuit with an expected value of the viscosity output signal based on a function of the temperature of the medium; and
   emitting a comparison output signal indicating a result of the comparing.

17. A process according to claim 16 wherein
a plurality of additional sensors determines other parameters of the medium and emits output signals compared to respective expected values.

18. A process according to claim 16 wherein
the expected value is a fixed value.

19. A process according to claim 16 wherein
the expected value is computed based on a pattern of temperature of the medium over time, and is variable.

20. A process according to claim 16 wherein
the expected value is stored in the evaluating circuit.

* * * * *